(12) United States Patent
Lewis et al.

(10) Patent No.: US 8,202,091 B2
(45) Date of Patent: Jun. 19, 2012

(54) DENTAL TREATMENT TRAYS COMPRISING SILICONE ELASTOMERIC MATERIAL

(75) Inventors: Paul Lewis, Midvale, UT (US); Scot N. Andersen, Draper, UT (US); Peter M. Allred, Riverton, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 538 days.

(21) Appl. No.: 12/201,902

(22) Filed: Aug. 29, 2008

(65) Prior Publication Data

US 2010/0055639 A1    Mar. 4, 2010

Related U.S. Application Data

(60) Provisional application No. 61/190,054, filed on Aug. 31, 2007.

(51) Int. Cl.
    *A61C 5/00*    (2006.01)
(52) U.S. Cl. ............................................. 433/215; 433/6
(58) Field of Classification Search ............... 433/6, 215
    See application file for complete search history.

(56) References Cited

U.S. PATENT DOCUMENTS

| | | |
|---|---|---|
| 165,584 A | 7/1875 | Hopfen |
| 1,637,153 A | 7/1927 | Lawton |
| 2,257,709 A | 9/1941 | Anderson |
| 2,833,278 A | 5/1958 | Ross |
| 2,835,628 A | 5/1958 | Saffir |
| 2,919,693 A | 1/1960 | Ross |
| 3,124,129 A | 3/1964 | Grossberg |
| 3,312,218 A | 4/1967 | Jacobs et al. |
| 3,339,547 A | 9/1967 | Drabkowski |
| 3,527,219 A | 9/1970 | Greenberg et al. |
| 3,577,640 A | 5/1971 | Lee |
| 3,624,909 A | 12/1971 | Greenberg et al. |
| 3,688,406 A | 9/1972 | Porter et al. |
| 3,923,754 A | 12/1975 | Pellico |
| 3,955,281 A | 5/1976 | Weitzman |
| 4,007,153 A | 2/1977 | Smith |

(Continued)

FOREIGN PATENT DOCUMENTS

AT    411146    10/2003

(Continued)

OTHER PUBLICATIONS

U.S. Appl. No. 12/183,303, filed Jul. 31, 2008, Lewis.

(Continued)

*Primary Examiner* — John J Wilson
(74) *Attorney, Agent, or Firm* — Workman Nydegger (57) ABSTRACT

Non-customized dental treatment trays used to provide a desired treatment are formed from elastomeric silicone or silicone-like material. They may be injection molded from a two-part liquid silicone composition or a silicone-like TPE material (e.g., preferably SEBS and/or VERSAflex thermoplastic elastomer). The dental treatment trays possess high adaptability, flexibility, softness, and elastic elongation while also exhibiting resiliency in order to readily conform to the ridges, depressions and contours of a person's teeth during use. The trays possess a greater ability to adhere to a person's teeth compared to non-elastomeric thermoplastic materials. Due to their high adaptability and conformability, the non-customized dental trays behave like a semi-custom dental tray when placed over conformed to a person's teeth, particularly when used in combination with a sticky, viscous treatment composition.

20 Claims, 5 Drawing Sheets

U.S. PATENT DOCUMENTS

| | | |
|---|---|---|
| 4,044,762 A | 8/1977 | Jacobs et al. |
| 4,063,552 A | 12/1977 | Going et al. |
| 4,064,628 A | 12/1977 | Weitzman |
| 4,138,814 A | 2/1979 | Weitzman |
| 4,161,067 A | 7/1979 | Bekey et al. |
| 4,591,341 A | 5/1986 | Andrews |
| 4,668,188 A | 5/1987 | Wolfenson et al. |
| 4,755,139 A | 7/1988 | Abbatte et al. |
| RE33,093 E | 10/1989 | Schiraldi et al. |
| 4,900,721 A | 2/1990 | Bansemir |
| 4,902,227 A | 2/1990 | Smith |
| 4,955,393 A | 9/1990 | Adell |
| 5,008,093 A | 4/1991 | Merianos |
| 5,035,613 A | 7/1991 | Breads et al. |
| 5,051,476 A | 9/1991 | Uji et al. |
| 5,055,039 A | 10/1991 | Abbatte et al. |
| 5,085,585 A | 2/1992 | Zimble |
| 5,108,742 A | 4/1992 | Merianos |
| 5,112,225 A | 5/1992 | Diesso |
| 5,135,392 A | 8/1992 | Polansky |
| 5,183,901 A | 2/1993 | Login et al. |
| 5,211,559 A | 5/1993 | Hart et al. |
| 5,224,958 A | 7/1993 | Warunek et al. |
| 5,268,396 A | 12/1993 | Lai |
| 5,310,563 A | 5/1994 | Curtis et al. |
| 5,326,685 A | 7/1994 | Gaglio et al. |
| 5,346,061 A | 9/1994 | Newman et al. |
| 5,356,291 A | 10/1994 | Darnell |
| 5,376,006 A | 12/1994 | Fischer |
| 5,409,631 A | 4/1995 | Fischer |
| 5,425,953 A | 6/1995 | Sintov et al. |
| 5,503,552 A | 4/1996 | Diesso |
| 5,513,988 A | 5/1996 | Jeffer et al. |
| 5,562,449 A | 10/1996 | Jacobs et al. |
| 5,566,684 A | 10/1996 | Wagner |
| 5,573,399 A | 11/1996 | McClintock, II |
| 5,575,654 A | 11/1996 | Fontenot |
| 5,611,687 A | 3/1997 | Wagner |
| 5,616,027 A | 4/1997 | Jacobs et al. |
| 5,631,000 A | 5/1997 | Pellico |
| 5,639,445 A | 6/1997 | Curtis et al. |
| 5,666,974 A | 9/1997 | Hiro et al. |
| 5,678,993 A | 10/1997 | Jeffer et al. |
| 5,702,251 A | 12/1997 | McClintock, II |
| 5,707,235 A | 1/1998 | Knutson |
| 5,711,935 A | 1/1998 | Hill et al. |
| 5,713,738 A | 2/1998 | Yarborough |
| 5,752,826 A | 5/1998 | Andreiko |
| 5,769,633 A | 6/1998 | Jacobs et al. |
| 5,807,100 A | 9/1998 | Thornton |
| 5,816,802 A | 10/1998 | Montgomery |
| 5,823,193 A | 10/1998 | Singer et al. |
| 5,846,058 A | 12/1998 | Fischer |
| 5,846,082 A | 12/1998 | Thornton |
| 5,851,512 A | 12/1998 | Fischer |
| 5,855,870 A | 1/1999 | Fischer |
| 5,863,202 A | 1/1999 | Fontenot et al. |
| 5,879,691 A | 3/1999 | Sagel et al. |
| 5,891,453 A | 4/1999 | Sagel et al. |
| 5,894,017 A | 4/1999 | Sagel et al. |
| 5,895,218 A | 4/1999 | Quinn et al. |
| 5,922,307 A | 7/1999 | Montgomery |
| 5,924,863 A | 7/1999 | Jacobs et al. |
| 5,952,400 A | 9/1999 | Hosoi et al. |
| 5,980,249 A | 11/1999 | Fontenot |
| 5,985,249 A | 11/1999 | Fischer |
| 5,989,569 A | 11/1999 | Dirksing et al. |
| 6,036,943 A | 3/2000 | Fischer |
| 6,045,811 A | 4/2000 | Dirksing et al. |
| 6,080,397 A | 6/2000 | Pfirrmann |
| 6,089,869 A | 7/2000 | Schwartz |
| 6,096,328 A | 8/2000 | Sagel et al. |
| 6,106,293 A | 8/2000 | Wiesel |
| 6,126,443 A | 10/2000 | Burgin |
| 6,136,297 A | 10/2000 | Sagel et al. |
| 6,142,780 A | 11/2000 | Burgio |
| 6,155,832 A | 12/2000 | Wiesel |
| 6,183,251 B1 | 2/2001 | Fischer |
| 6,197,331 B1 | 3/2001 | Lerner et al. |
| 6,247,930 B1 | 6/2001 | Chiang et al. |
| 6,251,966 B1 | 6/2001 | Fry et al. |
| 6,274,122 B1 | 8/2001 | McLaughlin |
| 6,277,458 B1 | 8/2001 | Dirksing et al. |
| 6,280,196 B1 | 8/2001 | Berghash |
| 6,287,120 B1 | 9/2001 | Wiesel |
| 6,306,370 B1 | 10/2001 | Jensen et al. |
| 6,309,625 B1 | 10/2001 | Jensen et al. |
| 6,312,671 B1 | 11/2001 | Jensen et al. |
| 6,322,360 B1 | 11/2001 | Burgio |
| 6,331,292 B1 | 12/2001 | Montgomery |
| 6,343,932 B1 | 2/2002 | Wiesel |
| 6,354,837 B1 | 3/2002 | Jensen |
| 6,364,665 B1 | 4/2002 | Trettemerp |
| 6,379,147 B1 | 4/2002 | Georgakis et al. |
| 6,386,865 B1 | 5/2002 | Suh et al. |
| 6,419,903 B1 | 7/2002 | Xu et al. |
| 6,419,906 B1 | 7/2002 | Xu et al. |
| 6,432,188 B1 | 8/2002 | Takai et al. |
| 6,435,873 B1 | 8/2002 | Burgio |
| 6,440,396 B1 | 8/2002 | McLaughlin |
| 6,458,380 B1 | 10/2002 | Leaderman |
| 6,461,158 B1 | 10/2002 | Sagel et al. |
| 6,488,914 B2 | 12/2002 | Montgomery |
| 6,497,575 B2 | 12/2002 | Zavitsanos et al. |
| 6,500,408 B2 | 12/2002 | Chen |
| 6,503,486 B2 | 1/2003 | Xu et al. |
| 6,506,053 B2 | 1/2003 | Wiesel |
| 6,514,483 B2 | 2/2003 | Xu et al. |
| 6,514,484 B2 | 2/2003 | Rajaiah et al. |
| 6,551,579 B2 | 4/2003 | Sagel et al. |
| 6,582,708 B1 | 6/2003 | Sagel et al. |
| 6,607,382 B1 | 8/2003 | Kuo |
| 6,638,496 B2 | 10/2003 | McLaughlin |
| 6,649,147 B1 | 11/2003 | Ye et al. |
| 6,682,721 B2 | 1/2004 | Kim et al. |
| 6,685,923 B2 | 2/2004 | Peterson et al. |
| 6,689,344 B2 | 2/2004 | Chang et al. |
| 6,730,316 B2 | 5/2004 | Chen |
| 6,765,038 B2 | 7/2004 | Mitra |
| 6,780,401 B2 | 8/2004 | Kim et al. |
| 6,884,426 B2 | 4/2005 | Sagel et al. |
| 6,945,778 B2 | 9/2005 | Jacobs et al. |
| 6,949,240 B2 | 9/2005 | Sagel et al. |
| 6,964,571 B2 * | 11/2005 | Andersen et al. .............. 433/215 |
| 7,040,897 B2 | 5/2006 | Fischer et al. |
| 7,048,543 B2 | 5/2006 | Allred et al. |
| 7,052,275 B2 | 5/2006 | Allred et al. |
| 7,056,118 B2 | 6/2006 | Allred et al. |
| 7,059,857 B2 | 6/2006 | Allred et al. |
| 7,059,858 B2 | 6/2006 | McLean et al. |
| 7,074,042 B2 | 7/2006 | Allred et al. |
| 7,094,393 B2 | 8/2006 | Montgomery |
| 7,114,953 B1 | 10/2006 | Wagner |
| 7,122,199 B2 | 10/2006 | Sagel et al. |
| 7,172,423 B2 | 2/2007 | Allred et al. |
| 7,192,280 B2 | 3/2007 | Allred et al. |
| 2001/0046654 A1 | 11/2001 | Zavitsanos et al. |
| 2002/0006387 A1 | 1/2002 | Sagel et al. |
| 2002/0006388 A1 | 1/2002 | Sagel et al. |
| 2002/0012685 A1 | 1/2002 | Sagel et al. |
| 2002/0018754 A1 | 2/2002 | Sagel et al. |
| 2002/0081555 A1 | 6/2002 | Wiesel |
| 2002/0164292 A1 | 11/2002 | Peterson et al. |
| 2002/0182154 A1 | 12/2002 | McLaughlin |
| 2002/0187111 A1 | 12/2002 | Xu et al. |
| 2002/0187112 A1 | 12/2002 | Xu et al. |
| 2003/0003421 A1 | 1/2003 | Bestenheider et al. |
| 2003/0012747 A1 | 1/2003 | Peterson et al. |
| 2003/0036037 A1 | 2/2003 | Zavitsanos et al. |
| 2003/0044631 A1 | 3/2003 | Sagal et al. |
| 2003/0068284 A1 | 4/2003 | Sagel et al. |
| 2003/0068601 A1 | 4/2003 | Zavitsanos et al. |
| 2003/0082114 A1 | 5/2003 | Kim et al. |
| 2003/0133884 A1 | 7/2003 | Chang et al. |
| 2003/0194382 A1 | 10/2003 | Chang et al. |
| 2003/0198606 A1 | 10/2003 | Kim et al. |
| 2003/0228264 A1 | 12/2003 | Perna |

| | | | |
|---|---|---|---|
| 2004/0005277 A1 | 1/2004 | Williston et al. | |
| 2004/0014006 A1 | 1/2004 | Garrison et al. | |
| 2004/0149292 A1* | 8/2004 | Fujieda et al. | 128/861 |
| 2005/0009972 A1 | 1/2005 | Rauh et al. | |
| 2005/0036957 A1 | 2/2005 | Prencipe et al. | |
| 2005/0048444 A1 | 3/2005 | Creamer | |
| 2005/0115571 A1 | 6/2005 | Jacobs | |
| 2005/0136381 A1 | 6/2005 | Andersen | |
| 2005/0214720 A1 | 9/2005 | Milanovich et al. | |
| 2005/0256276 A1* | 11/2005 | Elkin et al. | 525/400 |
| 2006/0130851 A1 | 6/2006 | Mathias | |
| 2006/0219250 A1* | 10/2006 | Farrell | 128/859 |
| 2006/0223033 A1 | 10/2006 | McLean et al. | |
| 2007/0003495 A1 | 1/2007 | Sagel et al. | |
| 2007/0037116 A1 | 2/2007 | Knutson | |
| 2007/0060717 A1 | 3/2007 | Zech et al. | |
| 2007/0166659 A1 | 7/2007 | Haase et al. | |
| 2007/0253990 A1 | 11/2007 | Sagel et al. | |
| 2007/0269471 A1 | 11/2007 | Sagel et al. | |

FOREIGN PATENT DOCUMENTS

| | | |
|---|---|---|
| DE | 3638888 | 5/1988 |
| EP | 1457167 | 9/2004 |
| GB | 2416310 | 1/2006 |
| GR | 1004634 | 7/2004 |
| JP | 61-225105 | 10/1986 |
| JP | 08/113520 | 7/1996 |
| JP | 2002-053418 | 2/2002 |
| JP | 2005-058594 | 10/2005 |
| KR | 20020045224 | 6/2002 |
| WO | WO 88/06869 | 9/1988 |
| WO | WO 03/000216 | 1/2003 |

OTHER PUBLICATIONS

"How Safe is Tooth Bleaching?", www.thefreelibrary.com/How+safe+is+tooth+bleaching%3F-a0118687915, based on information and belief available at least as early as Nov. 15, 2007.

"RevealSmile", www.reveal.com/services-we-offer/revealsmile, based on information and belief available at least as early as Nov. 15, 2007.

Play Safe Sport Brochure, Erkodent, published at least as early as Feb. 6, 2002, 1 pg.

ProTech Permafix, http://www.dentallabproducts.com/permafix.htm, Nov. 21, 2001, 4 pgs.

Hydro-Cast Dental Products, http://www.hydrocast.com/technique/68760.html, Nov. 21, 2001, 3 pgs.

Maxxgard, Mouthgard types, http://www.maxxgard.com/mouthguardtypes.html, Feb. 6, 2002, 2 pgs.

GC America, Inc., GC Reline™ Soft/Extra Soft, http://www.gcamerica.com/gcreline.html, Feb. 6, 2002, 2 pgs.

Hydro-Cast Dental Products, Mollosil® Plus, http://www.hydrocast.com/68760.html, Feb. 6, 2002, 2 pgs.

Types of Athletic Mouthguards, http://www.austindental.com/sports/mouthguards.shtml, Feb. 6, 2002, 4 pgs.

VOCO Scientific Information Denture Relining, Scientific Product Information, http://www.voco.com/usa/ufigelh/wi/wi_ug.htm, Feb. 6, 2002, 13 pgs.

Office Action dated Apr. 6, 2010 cited in U.S. Appl. No. 11/865,867.

Office Action dated Aug. 5, 2010 cited in U.S. Appl. No. 11/865,867.

Technical Bulletin: Hydrogen Peroxide-Polyvinylpyrrolidone Polymer Complexes, International Specialty Products, 1361 Alps Road, Wayne, New Jersey 07470, www.ispcorp.com (Dec. 2003).

U.S. Appl. No. 11/865867, filed Dec. 16, 2010, OA.

* cited by examiner

DENTAL TREATMENT TRAYS COMPRISING SILICONE ELASTOMERIC MATERIAL

CROSS REFERENCE TO RELATED APPLICATION

This application claims the benefit of U.S. Provisional Patent Application Ser. No. 61/190,054, filed Aug. 31, 2007 and entitled "DENTAL TREATMENT TRAYS AND STRIPS COMPRISING SILICONE" under 35 U.S.C. §119, the disclosure of which is incorporated by reference in its entirety.

BACKGROUND OF THE INVENTION

1. Field of the Invention

The invention is in the field of dental treatment trays used to deliver oral treatment compositions.

2. Background Technology

A common bleaching method involves the use of custom dental trays, which conform to the shape of each user's unique dentition. One way to form a customized tray is by vacuum forming a sheet of a moisture resistant thermoplastic polymer over a stone cast or model of a person's teeth and then trimming excess tray material. Another uses a person's teeth as the template (e.g., "boil-and-bite" trays). Customized dental trays prepared and sold by dentists are formed using a stone model of a patient's teeth and typically cost hundreds or even thousands of dollars.

Other methods involve flexible strips and non-customized trays and that can approximate differently sized and shaped dental arches and which are substantially less expensive than customized trays to manufacture. A dental bleaching composition is placed onto the strip or into the tray, which is then placed over the person's teeth for a desired period of time. To install a bleaching strip, a portion of the bleaching strip is placed over the front surfaces of the user's teeth, and the remainder is folded around the occlusal edges of the teeth and against a portion of the lingual surfaces. Because of the generally poor adhesion of bleaching strips to the user's teeth and their generally flimsy nature, it is often difficult for the user to maintain the bleaching strip in its proper position for the recommended time. Conventional bleaching strips are prone to slip off the teeth as a result of even minimal movement of the user's mouth, jaw or tongue. In some cases, the bleaching strip can become so dislodged or mangled that it must be removed by the user and replaced with a fresh bleaching strip to complete the recommended bleaching time.

Non-custom dental trays generally suffer from poor adaptability to the user's teeth. Although some non-custom dental trays are sufficiently flexible to generally adapt to differently sized and shaped dental arches within a certain range of sizes and shapes, existing non-custom trays, particularly trays that are used without an outer support tray and therefore must be self-supporting, are unable to comfortably adapt to dental arches of exaggerated size or shape (i.e., teeth that are unusually large, small or not particularly straight). Moreover, existing self-supporting trays have difficulty in adapting and conforming to the ridges, depressions and contours of a person's individual teeth in addition to adapting to the general shape and size of the person's dental arch. As a result of these failures, large gaps can easily form between the non-custom tray wall and the person's teeth during use, especially in the spaces between individual teeth, as a result of forming a bridge that spans between the outermost surfaces of adjacent teeth and/or the inability of the tray wall to accurately adapt to all the teeth in a row instead of simply accommodating the largest or most crooked teeth. Such gaps facilitate the invasion of saliva into the dental tray and/or expulsion of the dental bleaching composition from the dental tray during use.

Moreover, the inability of the front and rear walls of existing non-custom trays to adapt and conform to the ridges, depressions and contours of a person's individual teeth means that a substantial portion of each wall tends to move in unison as a result of external pressures (e.g., the person's lips or tongue pressing on the outer surface of a tray wall). Movement of a localized region of a self-supporting tray adjacent to one tooth typically causes simultaneous movement of the tray wall in adjacent regions where such movement may be undesired. In addition to forming large gaps, this may create a pumping action that exacerbates the aforementioned tendency of saliva to invade gaps between the tray walls and the person's teeth and/or bleaching composition to be expelled from the dental tray.

U.S. Pat. Nos. 6,964,571 and 7,004,756 ("Andersen patents") disclose self-supporting, non-custom dental trays made from thermoplastic materials such as low density polyethylene (LDPE), ultra low density polyethylene (ULDPE), ethylene-vinyl acetate copolymer (EVA), polycaprolactone (PCL), other types of polyethylene (PE), polypropylene (PP), polyesters, polycarbonates, polyamides, polyurethanes, polyesteramides, and copolymers thereof. The foregoing materials, when used to manufacture dental treatment trays that are relatively thick (i.e., greater than 2 mm), yield trays that are quite rigid and non-adaptable to the user's teeth absent customization. Therefore, Andersen discloses non-custom, self-supporting trays which are thin-walled (i.e., less than about 1 mm). This makes them sufficiently flexible so as to conform to a range of differently sized and shaped dental arches without the need for formal customization. While the self-supporting trays of Andersen represent an important advancement in the art compared to previously existing self-supporting dental trays, such trays do not readily and accurately adapt and conform to the ridges, depressions and contours of a person's individual teeth. Instead, they generally form a bridge between individual teeth that can span across the depressions between teeth. They also have tray wall regions that tend to move in partial unison rather than adapting themselves to the contours of individual teeth.

Moreover, the ability to injection mold dental trays from the types of thermoplastic materials disclosed in the Andersen patents is limited (i.e., there is a practical limit as to the thinness that such trays can be successfully injection molded). Accordingly, very thin-walled dental trays (i.e., less than about 5 mm) must be formed by other methods, such as vacuum forming a thin polymer sheet over a template.

In an attempt to improve upon the manufacturing process of Andersen, U.S. Pat. No. 7,137,814 ("Fischer patent") taught the inclusion of a substantial quantity (e.g., 20-50% by weight) of a hydrophobic oil plasticizer (e.g., mineral oil). The inclusion of a relatively large quantity of plasticizer greatly decreased the thickness at which dental trays could be injection molded. For example, trays having a wall thickness of less than about 0.015 inch (or about 0.4 mm) could, for the first time, be manufactured according to the Fischer patent. Moreover, the inclusion of a plasticizer such as mineral oil yielded dental trays that were softer and more flexible than dental trays made from non-plasticized thermoplastic polymers. Nevertheless, it was found that even hydrophobic plasticizers such as mineral oil tend to bloom (i.e., migrate to the surface) over time. Such blooming yields dental trays having poor taste and a surface to which hydrophilic dental bleaching compositions could not readily adhere. The inability of a sticky dental bleaching composition to readily adhere to the tray surface generally decreases adaptability and conformability of the tray to the person's teeth.

Ultimately, the main impediment to successful bleaching is the failure of users to complete the prescribed bleaching regimen. If the bleaching apparatus is difficult to install over a person's teeth, requires numerous repetitions to achieve observable results, or is uncomfortable to wear, the user may simply give up and prematurely abort the prescribed bleaching regimen. Thus, even if dental bleaching is possible using a particular bleaching apparatus or method, it is less likely to occur if the inadequacies of the bleaching apparatus or method cause a user to become discouraged before desired results are attained. One commercially successful pre-filled, self-supporting tray device manufactured according to Andersen has been a great success. Customer satisfaction has generally been high. Nevertheless, the main complaint of such devices is their inability to conform and adapt to the user's teeth like a custom tray.

As a result, the use of expensive customized dental trays remains the most reliable dental bleaching method in terms of regimen completion and results. Non-custom, over-the-counter bleaching strips and trays, while relatively inexpensive, generally provide inferior results compared to custom-fitting trays.

SUMMARY OF DISCLOSED EMBODIMENTS

The present invention generally relates to highly adaptable and conformable dental treatment trays used to deliver a dental treatment composition (e.g., a dental bleaching composition) to a person's teeth. Because the non-custom trays are highly adaptable, they readily and accurately adapt and conform to the ridges, depressions and contours of a person's individual teeth. They are also able to conform and adapt to a wide variety of differently sized and shaped dental arches, even those of exaggerated size and shape. This is true even when the trays are designed so as to be self-supporting. When in use, the highly adaptable and conformable dental treatment trays yield what may be characterized as a "semi-custom dental tray". The result is a non-custom dental tray which is more comfortable and adapts to a user's teeth more like a customized dental tray than any existing dental tray or treatment strip. And unlike dental strips, which more easily become dislodged than a tray during use, the highly adaptable dental trays, while soft and extremely comfortable to wear, have sufficient elastic qualities as to remain in the shape of a tray during use. This greatly improves their ability to remain in place during treatment compared to conventional bleaching strips made from thin, flexible thermoplastic polymer sheets.

Embodiments of the disclosed non-custom dental treatment trays are formed from elastomeric silicone or other highly elastomeric material which exhibits properties similar to silicone (e.g., styrene-ethylene-butylene-styrene (SEBS) and VERSAflex, a proprietary thermoplastic elastomer alloy that exhibits elastic elongation and other properties similar to silicone). VERSAflex is sold by GLS Corporation, based in McHenry, Ill. SEBS and VERSAflex are especially useful examples of thermoplastic elastomers exhibiting properties similar to silicone and may hereafter be referred to as "elastomeric silicone-like materials". The terms "elastomer" and "elastomeric silicone-like materials" include thermoplastic and thermoset materials.

Because the disclosed trays are made from highly elastomeric materials, they readily elongate elastically. It is this property of high elastic elongation, which is absent in non- or low-elastomeric thermoplastic polymers used to make conventional trays and strips, that permits the disclosed trays to more closely adapt to the ridges, depressions and contours of a person's teeth and also dental arches of greatly varying size and shape.

Unlike conventional thermoplastic materials used to form boil and bite dental trays, neither elastomeric silicone nor "elastomeric silicone-like materials" can be sufficiently softened by boiling in water to form a customized dental tray. Indeed, heating generally does not soften non-custom dental trays comprised of cured silicone or other thermoset elastomers, as they are not thermoplastic materials. Thermoplastic elastomers generally only become softened at temperatures that are much higher than the boiling point of water. Such materials cannot be made into customized dental trays in this manner. The non-custom dental trays therefore exhibit much greater thermal stability compared to conventional thermoplastic tray and strip materials.

Elastomeric materials exhibit excellent adaptability, flexibility, elastic elongation, and softness, while also exhibiting resiliency (i.e., the ability to spring back to its original configuration upon release of a deforming force). Such a combination of properties results in a high level of form fitting and user comfort. Because dental trays formed of highly elastomeric silicone or silicone-like materials exhibit such beneficial characteristics even with higher wall thicknesses, they can have an added advantage of reduced flimsiness compared to thinner walled trays and strips, making them easier to place. In other words, dental treatment trays made from an elastomeric silicone or an elastomeric silicone-like material and having a given wall thickness will exhibit greater adaptability, flexibility, and softness than trays of the same thickness formed from thermoplastic materials commonly used to manufacture existing dental trays. In addition, the disclosed trays exhibit excellent elastic elongation and resiliency, which are lacking in existing non-custom dental trays and strips made from thermoplastic polymers, even if a substantial quantity of a plasticizer is added (i.e., a plasticizer can soften a thermoplastic material but cannot convert it into an elastomer).

Elastomeric silicone and silicone-like materials also exhibit greater surface adhesion compared to thermoplastic materials used to manufacture conventional dental trays and strips. This increased surface adhesion further increases adaptability as the disclosed dental trays can more readily adhere to a person's tooth surfaces and/or a sticky, viscous dental treatment composition positioned adjacent to a surface of the trays. The surface adhesion of dental trays made from elastomeric silicone and silicone-like materials, particularly when used with a sticky, viscous dental bleaching composition, further enhances adaptability and conformability of the trays compared to conventional trays. For example, conventional non-custom dental trays can move relative to the teeth, causing ingress of saliva and/or egress of dental treatment composition. Even more egregiously, conventional dental bleaching strips are notoriously non-adhesive to teeth and readily slip off and/or easily become mangled and virtually unusable during use. Providing trays made from elastomeric silicone and silicone-like materials provides a substantial improvement over conventional trays and strips relative to their ability to stay in place during use.

Although elastomeric silicone and silicone-like materials are generally more expensive than conventional thermoplastic materials, they result in a net savings in manufacturing cost when the overall cost is considered. Thermoplastic materials are difficult to injection mold, especially at very thin cross sections (i.e., less than 0.5 mm), which means that conventional dental trays are typically formed by molding and/or cutting from a sheet material. This greatly complicates the manufacturing process. Forming dental trays by injection molding greatly reduces the cost. Moreover, the inventors' practical experience has shown that labor costs in manufacturing relatively comfortable thin walled (e.g., less than about 0.4 mm) dental treatment trays from plasticized thermoplastic materials are so significant that costs savings and improved characteristics can be realized by forming dental trays from elastomeric silicone or silicone like materials. The ability to injection mold more expensive silicone and other elastomeric materials into dental trays, while reducing overall manufacturing costs compared to forming trays from less expensive non-elastomeric thermoplastic polymers, is a surprising and unexpected result.

In general, elastomeric silicone and silicone-like materials can be injection molded while using little or no plasticizer. Thus, according to one embodiment, dental trays can be formed of a material which consists essentially or exclusively of silicone or other elastomeric material. Eliminating plasticizers greatly simplifies manufacture, as only the silicone material (e.g., provided as a medical grade thermoset two-part liquid composition) is required. Eliminating the plasticizer also eliminates plasticizer bloom, which improves taste and enhances adhesion of the molded trays to teeth and dental treatment compositions.

Although SEBS, VERSAflex, and other exemplary thermoplastic elastomers can be mixed with small quantities of auxiliary components, such other materials will generally constitute less than about 10% by weight, preferably less than about 5% by weight, more preferably less than about 3% by weight, even more preferably less than about 1% by weight, and most preferably 0% by weight of the composition used to manufacture dental trays.

When used to deliver a dental treatment composition to a person's teeth, and when it is desired to maximize adaptability, conformability and comfort, the disclosed dental trays will generally have a wall thickness less than about 1 mm, preferably in a range of about 0.03 mm to about 1 mm, more preferably in a range of about 0.05 mm to about 0.75 mm, and most preferably in a range of about 0.1 mm and about 0.5 mm.

Dental trays having a wall thickness greater than 1 mm are generally less comfortable and adaptable then the more preferred thinner walled dental trays. That is particularly true when using an elastomeric material having the same shore A hardness. Nevertheless, unlike thermoplastic materials used to make conventional dental trays, the shore A hardness of elastomeric materials can be more easily manipulated (e.g., reduced) in order to yield thicker walled dental trays that still have high adaptability and conformability to a user's teeth. Hence, dental trays having a thickness greater than 1 mm (e.g. up to about 1.5 mm) but which still exhibit high adaptability, conformability and comfort, are within the scope of the invention.

The durometer hardness/softness of the elastomeric silicone or other elastomeric materials is advantageously selected to strike a balance between softness and wall thickness. Within the preferred wall thicknesses described above (i.e., about 0.03 mm to about 1 mm) the shore A durometer hardness value will preferably range from about 90 to about 20. Generally, a higher durometer value (less softness) is preferred when making thinner wall trays (e.g., in order to maintain good resiliency and spring-back properties), while lower durometer values (greater softness) are preferred with thicker wall trays (e.g., in order to maintain softness, high adaptability and comfort). For example, a tray with a wall thickness of about 0.25 mm may advantageously have a shore A durometer hardness value of about 40, while a tray with a wall thickness of about 0.1 mm may have a shore A durometer hardness value of about 70. On the other hand, a non-custom dental tray having a thickness of 1.5 mm may advantageously have a shore A hardness of about 10.

The dental treatment trays disclosed herein are not customized. That is, before they are placed over a user's teeth, they lack indentations or other features corresponding to the user's unique dentition. In this way they are able to adapt to and fit the contours of a wide variety of differently sized and shaped dental arches. Nevertheless, because the dental trays disclosed herein are extremely adaptable and conformable, particularly when used in combination with a dental treatment composition that is sticky and adhesive like a glue, once placed over the user's teeth and manipulated so as to conform to ridges, depressions and contours of the user's teeth (e.g., by pressing with fingers and or the user's lips), the non-custom dental trays will perform much like a customized tray. While in use, they may be considered to be a semi-custom tray. However, they are not "customized" in the conventional sense of this term because, when removed from the user's teeth, they will still lack indentations or other features corresponding to the user's unique dentition and could (at least in theory if sanitation were not a concern) be used on another person's teeth and exhibit the same semi-customized feel and performance. The ability of the highly adaptable and conformable non-custom dental trays disclosed herein to behave as semi-custom dental trays when in use while remaining non-customized is a surprising and unexpected result compared to conventional non-customized dental trays made from non-elastomeric thermoplastic polymers.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Preferred embodiments of the invention include highly adaptable dental treatment trays used to deliver a dental treatment composition (e.g., a dental bleaching composition) to a person's teeth. Preferred trays are highly adaptable and readily and accurately adapt and conform to the ridges, depressions and contours of a person's individual teeth and also a wide variety of differently sized and shaped dental arches. When in use, the highly adaptable and conformable trays may be characterized as "semi-custom dental trays".

Surprisingly and unexpectedly, trays formed from elastomeric silicone or silicone-like material have much greater adaptability conformability (i.e., the ability of a non-custom tray to be shaped and adapted to conform to the ridges, depressions and contours of a person's individual teeth during use) as compared to conventional thermoplastic materials used to make trays (e.g., EVA materials), while also providing increased resiliency (i.e., the ability of the tray structure to spring back into place). As a result, non-custom dental trays made from thermoset elastomeric silicone, other thermoset elastomers, or thermoplastic elastomers can greatly improve the bleaching experience and better ensure regimen compliance compared to existing pre-filled dental trays and bleaching strips.

Surprisingly and unexpectedly, the disclosed trays can much more closely approximate the experience of using a customized dental tray but at a tiny fraction of the cost of manufacturing a customized dental tray, which requires taking an impression of each patient's teeth, forming a stone model for each patient, and then forming a customized tray from the stone model for each patient. In contrast, non-customized trays as disclosed herein can be mass-produced (e.g., by injection molding) in order to fit a wide variety of differently sized and shaped teeth and dental arches.

Another surprising and unexpected feature is the ability of the disclosed dental trays to exhibit greater adaptability and conformability to a person's teeth, even when having thicker walls, compared to thinner-walled non-custom dental trays made from conventional thermoplastic polymers that have little or no elastomeric properties. This provides the added advantage of reduced flimsiness, making the disclosed trays easier to place (i.e., they can easily be placed without the assistance of an outer support tray) and remain in place. Stated another way, an elastomeric silicone or silicone like dental treatment tray having a given wall thickness will exhibit adaptability, flexibility, and softness that are at least as good, and typically significantly greater than, a thinner tray formed of conventional thermoplastic materials (e.g., EVA). In addition, dental trays made from elastomeric silicone or silicone-like materials exhibit resiliency and elastic elongation, which qualities are lacking in trays formed of other materials. The unique combination of properties increases the comfort to the user, which increases compliance with a given treatment regimen.

In contrast to trays made from non-elastomeric polymers, which do not elastically elongate during use and therefore tend to form bridges that span across the gaps between individual teeth, the disclosed trays have high elastic elongation, which permits them to more closely adapt and conform to the valleys, depressions and contours of a person's individual teeth. No matter how flexible a non-elastomeric polymer tray may be, if it cannot elastically elongate, it cannot adapt to the depressions between some teeth without being dislodged from and/or stretched like a bridge across other teeth. As compared to existing of non-custom dental trays, the disclosed trays can easily adapt and conform to the valleys, depressions and contours of some teeth without being dislodged and/or stretched like a bridge across other teeth. This is a surprising and unexpected result as compared to existing non-custom dental trays.

Figure 1:
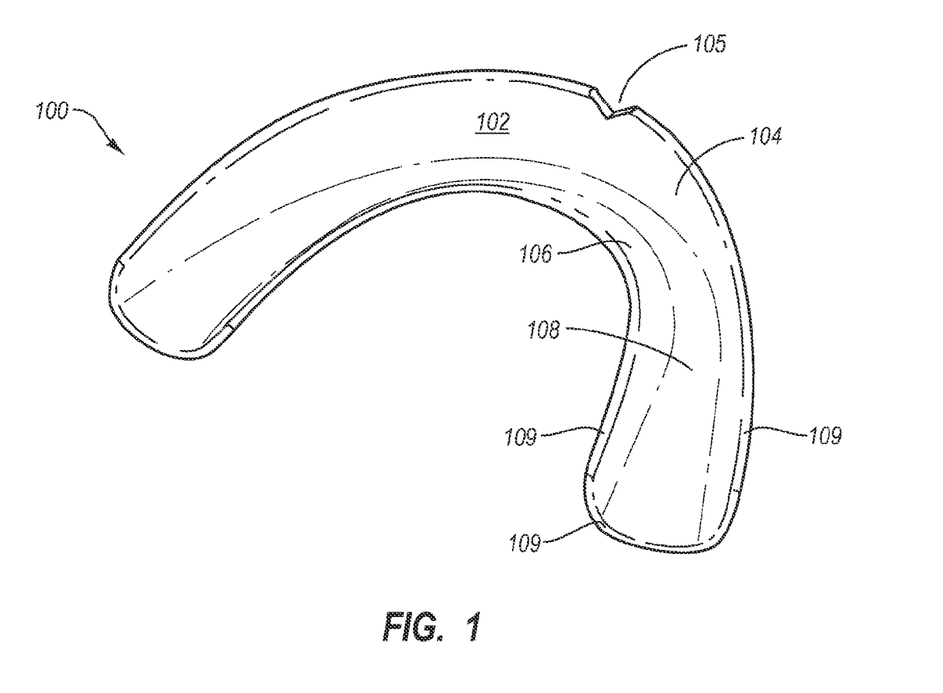
FIG. 1 is a perspective view of an exemplary non-custom dental treatment tray according to the invention.

II. Exemplary Dental Trays Made From Elastomeric Silicone and Silicone-Like Materials FIG. 1 illustrates an exemplary non-custom dental tray 100 which may be formed by liquid injection molding an elastomeric silicone or silicone-like material. For example, an elastomeric silicone material may initially comprise a two-part composition including a first part comprising one or more siloxanes and a second part including an activator. Upon mixing the two liquid parts together, the siloxane component polymerizes and cross-links so as to form a polysiloxane. Heat may be applied (e.g., by heating the mold) to accelerate polymerization of the elastomeric silicone material. For example, part A and part B of the raw silicone material are mixed together, which causes the silicone to begin to polymerize. For many exemplary silicone materials, this reaction could take 2-6 weeks to completely cure at room temperature. This provides sufficient time to injection mold or otherwise shape the mixed silicone material into a desired shape of a non-custom tray, which processes may involve heating the shaped material to more rapidly cure the silicone material once positioned into the desired shape. Heating the mixture significantly increases the rate at which the material polymerizes. According to an exemplary method, the shaped silicone material can be heated to about 375° F., which can cause the silicone material to polymerize in a matter of seconds. Actual polymerization time depends on the particular silicone product as well as the thickness of the tray being formed. The inventive trays may also be cured by other methods, for example in which polymerization of a two part silicone is activated by mixing and/or by compression.

Dental treatment tray 100 includes a shaped tray body 102. The shaped tray body 102 includes a buccal-labial front side wall 104, a lingual rear side wall 106, and a bottom wall 108 bridging the buccal-labial wall 104 and lingual wall 106. Bottom wall 108 is adjacent to buccal-labial wall 104 such that buccal-labial wall 104 extends laterally from bottom wall 108 in a substantially vertical direction. Lingual wall 106 is disposed at the opposite side of bottom wall 108, extending laterally upwardly and outwardly therefrom. The buccal-labial wall 104, lingual wall 106, and bottom wall 108 together form a shaped tray body 102 having an approximate U-shaped cross section and a generally horseshoe-shaped curvature. An alternative L-shaped tray may include a buccal-labial side wall and a bottom wall adjacent the buccal-labial side wall.

Buccal-labial wall 104 and lingual wall 106 may include rounded edges 109 in order to maximize comfort of the tray compared to trays having sharper or more abrupt edges. Buccal-labial wall 104 may include an optional V-shaped cut 105 formed along the top surface thereof, near the center where the incisors reside during use. V-shaped cut 105 helps wall 104 to stretch and flex so as to better accommodate the incisors. Although not shown, such a similar cut or discontinuity may be formed within lingual wall 106.

The size, shape and curvature of the shaped tray body 102 are advantageously selected in order for the horseshoe-shaped curvature to generally approximate the curvature of a person's dental arch. The U-shaped cross section generally corresponds to and defines an interior cavity of the tray body 102. The depth of the interior cavity is selected in order for the buccal-labial and lingual walls 104 and 106 respectively to extend over a desired portion of a person's teeth, and optionally, over a portion of the person's gums. Because of the excellent adaptability, conformability, flexibility, elastic elongation, and resiliency afforded by elastomeric silicone or silicone-like materials from which shaped tray body 102 is formed, the ability of buccal-labial wall 104, lingual wall 106, and bottom wall 108 to conform and adapt to a person's teeth is substantially increased relative to non-custom trays formed of non-elastomeric thermoplastic materials.

Because of its non-custom nature (i.e., tray body 102 is substantially devoid of structures corresponding to the size and shape of a person's unique dentition), the body 102 comfortably fits over a plurality of differently sized and/or shaped teeth corresponding to different people. Nevertheless, it is within the scope of the invention to provide differently sized dental trays sized and configured to correspond to a person's upper and lower dental arches, as the lower dental arch is typically smaller than the upper arch, with lower teeth that are typically smaller than the upper teeth. It is also within the scope of the invention to provide varyingly-sized treatment trays to account for variability among different people's dental arches and/or teeth (e.g., adults versus children, larger mouths versus average or smaller mouths, and larger teeth versus average or smaller teeth).

The tray body 102 may be injection molded, vacuum formed, cut and/or stamped from a sheet of silicone or silicone like material, although injection molding is preferred over other methods that involve cutting and/or stamping because the outer edges 109 of each wall may be molded so as to have a smooth, rounded edge surface as opposed to the sharp, angled surfaces formed when a tray is cut or stamped from a sheet of material. Such smooth edges also contribute to the overall comfortable feel of the tray, adding to the increased comfort offered by the silicone or silicone like material from which body 102 is formed.

Figure 2A:
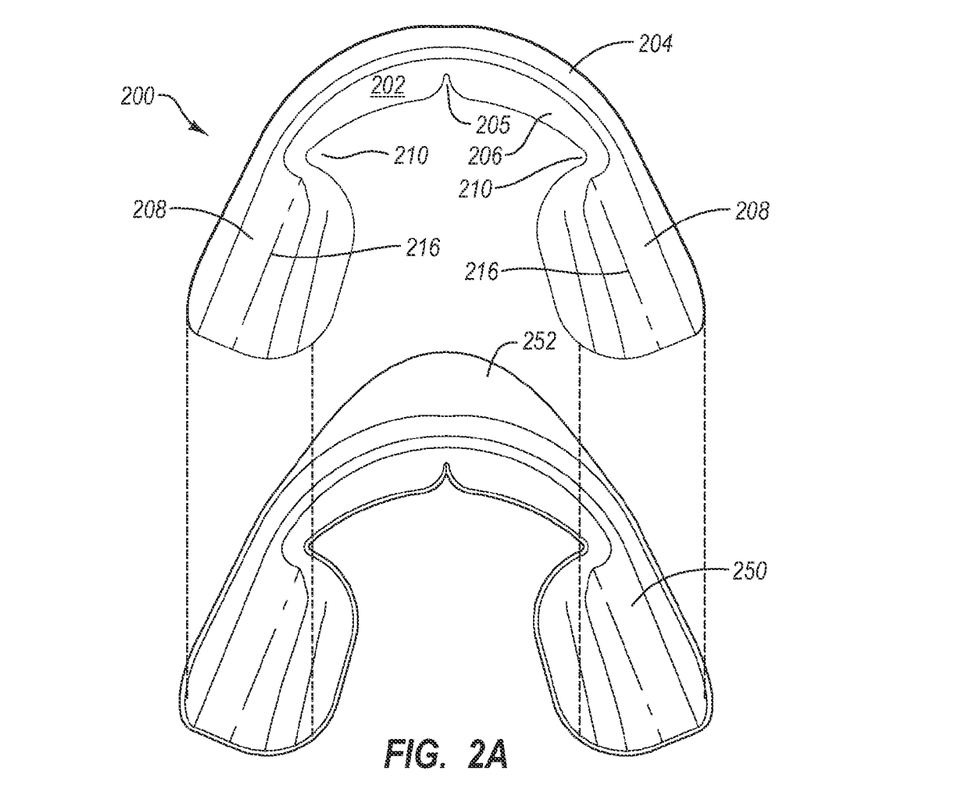
FIG. 2A is an exploded view of an alternative dental treatment tray including anatomical features for enhanced fit along with an optional complementary outer support tray.

FIG. 2A illustrates an alternative non-custom dental treatment tray 200 that includes non-custom anatomical features that allow tray 200 to more closely conform to a person's teeth during use. Body 202 includes a buccal-labial front side wall 204, a bottom wall 208, and a lingual side wall 206 connected to bottom wall 208 at an opposite side relative to buccal-labial wall 204. Illustrated tray 200 is sized and configured for placement over a person's upper dental arch. As illustrated, lingual wall 206 may advantageously include a notch 205, which allows the non-custom tray 200 to more easily spread open or compress in the area of the incisors. This is helpful in allowing the lingual wall 206 of the non-custom tray 200 to more easily conform to differently-sized dental arches. Bottom wall 204 includes an abrupt reduction in width at locations 210 corresponding to a transition between posterior teeth (i.e., bicuspids and molars) and anterior teeth (i.e., canines and incisors). Bottom wall 208 also advantageously includes two V-shaped indentations 216 for insertion into the depression between the occlusal peaks of the posterior teeth (i.e., the bicuspids and molars).

Figure 2B:
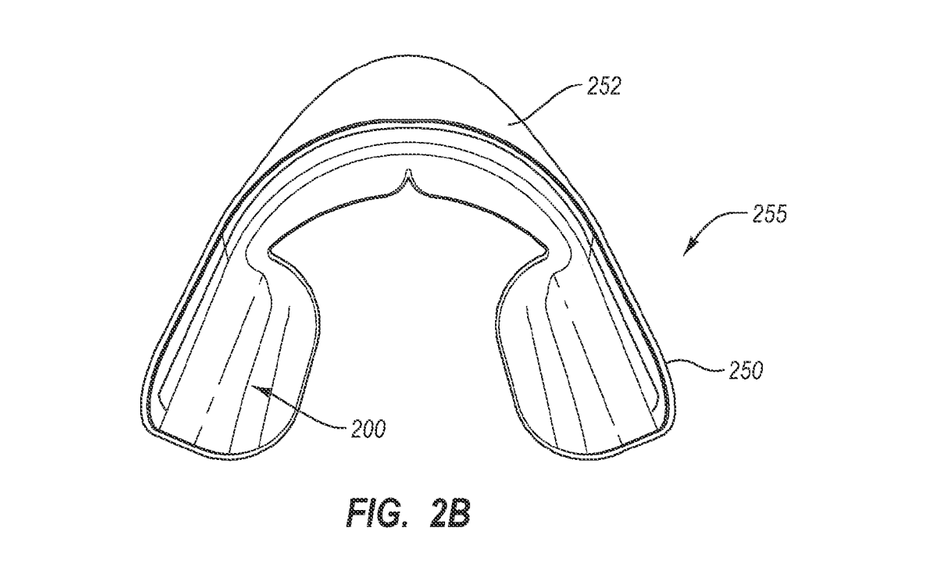
FIG. 2B is a perspective view showing the dental treatment tray of FIG. 2A nested within the outer support tray of FIG. 2A.

FIG. 2A is an exploded view showing the dental bleaching tray 200 in combination with a corresponding optional outer support tray 250 that is complementarily shaped so as to be capable of receiving the dental bleaching tray 200 in a nested configuration (see FIG. 2B). The outer support tray 250 may include the same anatomical features as tray 200 in order to provide a closer fit. The outer support tray 250 advantageously includes a handle 252 extending outwardly from a central portion of the buccal-labial front wall in order to facilitate gripping by the user during placement of the dental bleaching tray 200 over the person's teeth.

In FIG. 2B, dental bleaching tray 200 is nested within outer support tray 250 so as to form a dental tray assembly 255. The handle 252 extends beyond the buccal-labial wall of tray 200 in order to facilitate placement and removal of the outer support tray 250 after placement of tray 200 over the person's teeth.

Of course, the dental trays within the scope of this disclosure may advantageously be formed with sufficient self-supporting integrity (i.e., they are not so flimsy that the side wall(s) collapse inwardly) so that no outer support tray or other supporting structure is required. Relatively thick trays (e.g., at least about 0.45 mm) may be formed so as to exhibit a lower shore A durometer hardness value (e.g., no more than about 40) for increased softness to balance increased wall thickness and provide an overall comfortable fit. Relatively thick trays advantageously exhibit excellent adaptability, resiliency, softness, flexibility, and comfort which is greater than a similarly sized tray formed of, for example an EVA/PP and plasticizer blend.

In one embodiment, a non-custom dental tray comprising an elastomeric silicone or silicone-like material may be pre-packaged with a dental treatment composition pre-loaded within the tray. In order to protect the tray and the treatment composition pre-loaded therein, the dental treatment tray can be packaged within a sealed container or package to protect the tray and particularly the treatment composition from contaminants during storage and prior to use.

Figure 3:
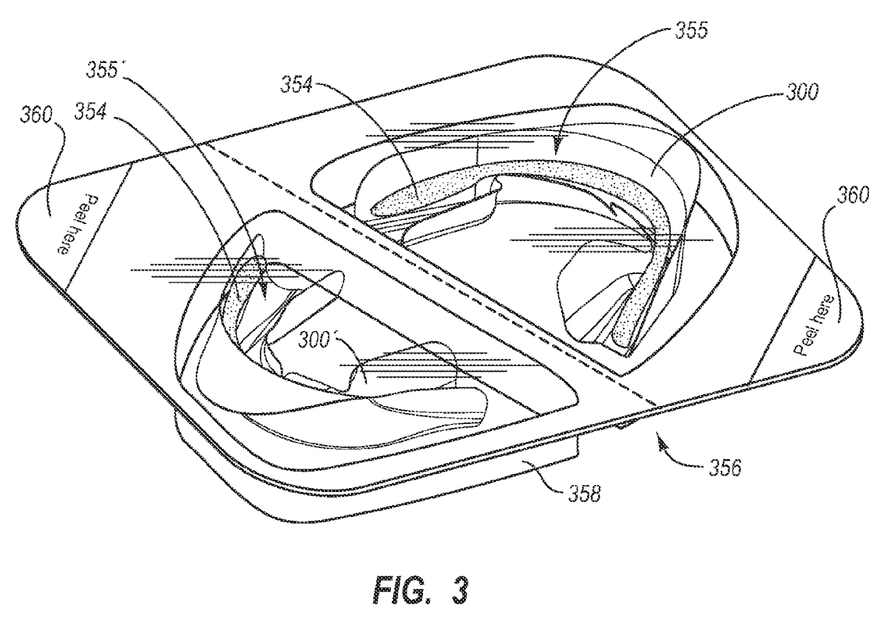
FIG. 3 illustrates a pair of tray assemblies similar to the assembly of FIG. 2B contained within a sealed protective package having a peelable cover.

FIG. 3 shows a tray assembly 355 configured for placement over an upper dental arch and a tray assembly 355' configured for placement over a lower dental arch sealed within protective package 356. Each tray 300 and 300' includes a treatment composition 354 pre-loaded therein. Protective package 356 includes a rigid support layer 358 and a peelable cover 360. Each tray assembly 355 and 355' may optionally include a removable protective layer (not shown) placed adjacent to the treatment composition 354 for additional protection. When it is desired to use the dental treatment tray devices, the peelable cover 360 is removed and the tray assemblies 355 and 355' are removed or separated from support layer 358.

Alternatively, the dental trays disclosed herein may be provided separately from a dental treatment composition, which is later introduced into the tray by the user immediately prior to use. For convenience, one or more non-custom dental treatment trays, or tray assemblies comprising treatment trays nested within outer support trays, may be provided in a kit along with one or more dental treatment compositions.

Examples of treatment compositions include dental bleaching compositions (e.g., including a dental bleaching agent such as a peroxide), desensitizing compositions (e.g., including a desensitizing agent such as potassium nitrate, other potassium salts, citric acid, citrates, and/or sodium fluoride), remineralizing compositions (e.g., including a remineralizing agent such as sodium fluoride, stannous fluoride, sodium monofluorophosphate, and/or other fluoride salts), antimicrobial compositions (e.g., including an antimicrobial agent such as chlorhexidine, troclosan, and/or tetracycline), antiplaque compositions, and anti-tartar compositions (e.g. including an anti-tartar agent such as a pyrophosphate salt). The treatment composition may comprise a sticky viscous gel, a less viscous gel, a highly viscous putty, or a substantially solid composition that is less adhesive prior to being moistened with saliva or water but that becomes more sticky and adhesive when moistened.

In the case of a silicone tray preloaded with an aqueous peroxide-containing dental bleaching composition, it may be necessary to include a rupturable membrane layer (e.g., which is configured to rupture upon biting, bending, and/or flexing) between a pre-loaded composition and the silicone tray to prevent premature decomposition of the peroxide bleaching agent as a result of contact with residual platinum and/or tin catalyst present within the silicone material. Alternatively, the rupturable membrane layer may be water-degradable so as to dissolve, degrade, or become dispersed upon contact with moisture (e.g., saliva).

Advantageously, the tray consists essentially of elastomeric silicone or a silicone-like material, as this has been found by the inventors to provide the most beneficial combination of properties, including excellent adaptability, flexibility, softness, and elastic elongation, while also exhibiting excellent resiliency. Although it is preferred that the moisture resistant polymer material of the tray body consist solely of silicone or one or more silicone-like materials, it may be possible in some embodiments to include additional moisture resistant polymer components so that the material comprises a blend of elastomeric silicone or silicone-like materials and other materials. Additional materials that may be included in such an example include one or more elastomers (e.g., a non-silicone like thermoplastic elastomer), latexes, and/or nitrites. Preferably, any such additional moisture resistant components comprise no more than about 10% by weight of the tray, more preferably no more than about 5%, more preferably not more than about 3% by weight, and most preferably no more than about 1% by weight.

Additional components such as water and/or a plasticizer (e.g., PEG), a colorant, and/or a flavorant may be added to the composition from which the tray body is formed, although addition of such materials is typically unnecessary and less preferred. Similarly, addition of any such components are in very small amounts (e.g., no more than about 10% by weight, more preferably no more than about 5% by weight, more preferably no more than about 3% by weight, most preferably no more than about 1% by weight).

Exemplary suitable two-part silicone materials are available from Shin-Etsu Silicones of America, located in Akron, Ohio. One preferred material is KEG2000-50A/B, the physical properties of which are described in the table below. Various other Shin-Etsu silicone products and silicone materials from other suppliers can also be used.

| Property | Value |
| --- | --- |
| Hardness - Shore-A | 52 |
| Tensile Strength - MPa | 11.1 |
| Elongation - % | 580 |
| 100% Modulus - MPa | 1.72 |
| Tear Strength - kN/m | 40 |
| Comp Set 22 h/302° F.-1 h/302° F. | 31 |
| Comp Set 22 h/302° F.-4 h/392° F. | 8 |
| Linear Shrinkage | 2.6 |
| Specific Gravity | 1.13 |
| Viscosity - Part A-Pa·s | 1700 |
| Viscosity - Part B-Pa·s | 1600 |

A suitable example of a SEBS material is SEBS TPE 45A, available from various providers. Physical properties for SEBS TPE 45A are summarized in the table below. Various other SEBS products may also be used.

| Property | Value |
| --- | --- |
| Density (g/cm$^3$) | 0.94 |
| Surface Hardness - Shore A | 45 |
| Tensile Strength (MPa) | 6 |
| Flexural Modulus (GPa) | 0.02 |
| Notched Izod (kJ/m) | 1.06+ |
| Linear Expansion (/° C. × 10$^{-5}$) | 16 |
| Elongation at Break (%) | 800 |
| Water Absorption (%) | 0.3 |

| Property | Value |
| --- | --- |
| Oxygen Index (%) | 19 |
| Melting Temp. Range (° C.) | 200-240 |
| Mold Shrinkage (%) | 1.5 |
| Mold Temp. Range (° C.) | 50-70 |

Several suitable VERSAFLEX TPE materials are available from GLS Corporation, located in McHenry, Ill. Preferred VERSAFLEX materials include VERSAFLEX CL30 and VERSAFLEX CL40, properties of each of which are summarized in the table below. Various other VERSAFLEX products from GLS Corporation can also be used.

| | Product | | |
| --- | --- | --- | --- |
| Property | VERSAFLEX CL30 | VERSAFLEX CL40 | Test Method |
| Shore A Hardness, 10 sec delay | 30 | 43 | ASTM D2240 |
| Specific Gravity | 0.89 | 0.89 | ASTM D792, 23/23° C. |
| Tensile Strength | 6619 kPa | 5929 kPa | ASTM D412-Die C, 2 hrs, 23° C. |
| Elongation at Break | 780% | 690% | ASTM D412-Die C, 2 hrs, 23° C. |
| 100% Modulus | 689 kPa | 1379 kPa | ASTM D412-Die C, 2 hrs, 23° C. |
| 300% Modulus | 1448 kPa | 2413 kPa | ASTM D412-Die C, 2 hrs, 23° C. |
| Tear Strength | 19 kN/m | 23 kN/m | ASTM D624 |
| Melt Flow Rate @ 190° C., 2160 g | 18 g/10 min | 13 g/10 min | ASTM D 1238 |
| Melt Flow Rate @ 200° C., 5000 g | 108 g/10 min | 38 g/10 min | ASTM D 1238 |
| Apparent Viscosity @ 200° C. 11170/sec | 15 Pa-s | 16 Pa-s | ASTM D 3835 |
| Compression Set, 22 hrs @ RT | 11% | 12% | ASTM D 395B |

Examples of additional elastomeric silicone and silicone-like materials that may be used are listed in the table below. It is noted that the silicone-like materials listed below differ in their properties from materials used previously in the manufacture of dental treatment trays. For example, although different EVA materials have been used in the manufacture of dental treatment trays previously, the EVA materials noted in the table below (i.e., Ateva 2810A and Evatane 33-400) exhibit elastomeric silicone-like properties (e.g., particularly elastic elongation, softness, and resiliency) which properties are markedly different from conventional EVA materials used previously in the manufacture of dental treatment trays which are only superficially similar. For example, it is noted that each of the materials listed below have an elasticity (i.e., elastic elongation) of at least about 300 percent, more typically between about 450 percent and about 800 percent. As described above, the elastic elongation, resilience and softness of such materials provides a "feel" and resulting performance very much like elastomeric silicone.

| Manufacturer | Product | Product Type | Shore A Hardness | % Elongation |
|---|---|---|---|---|
| Shin-Etsu | SVX-19550C-7 | Silicone | 50 | 640 |
| Wittenburg B.V. | MT 970 | SEBS | 70 | |
| Wittenburg B.V. | Cawiton PR 2677F | SEBS | 25 | |
| Teknor Apex | MP 1870-1000 | SEBS-TPE | 70 | 600 |
| Bayer | Texin 985 | TPE (Polyether) | 86 | 500 |
| Bayer | Texin 285 Natural | TPE (Polyether) | 85 | 500 |
| Bayer | Texin 1201 | TPE | 67 | 300 |
| GLS Corp. | Versaflex - CL 30 | TPE | 30 | 780 |
| GLS Corp. | Versaflex - CL 40 | TPE | 43 | 690 |
| GLS Corp. | Versaflex 2250 | TPE | 50 | 760 |
| GLS Corp. | Versalloy 9055X-1 | TPE | 53 | 590 |
| GLS Corp. | Dynaflex G2701-1000-02 | TPE | 66 | 590 |
| GLS Corp. | Dynaflex G 2703-1000-02 | TPE | 58 | 690 |
| Dow Corning | TPSiV 3010 | TPE | 50 | 470 |
| Dow Corning | TPsiV 3040-55A | TPE | 55 | 450 |
| Dow Corning | LSR C6-550 | Silicone | 55 | 661 |
| Dow Corning | LSR C6-570 | Silicone | 70 | 442 |
| Dow Corning | Silastic Dev SB 2% bleed | Silicone | 50 | 450 |
| JRS | Excelink 1600B | TPE | 56 | 640 |
| PolyOne | Elastamax EG-9065 | TPE | 65 | 420 |
| Advance Polymers | Duragrip DGR 6250 CL | TPE | 50 | 800 |
| Elastocon | Elastocon 2840 | TPE | 40 | 580 |
| Elastocon | Elastocon 2855 | TPE | 55 | 660 |
| Kraiburg | Thermolast TF4THT | TPE | 40 | 610 |
| Kraiburg | Thermolast TF5THT | TPE | 50 | 680 |
| Kraiburg | Thermolast TF6THT | TPE | 60 | 710 |
| AT Plastics | Ateva 2810A | EVA-C | 79 | 820 |
| Arkema | Evatane 33-400 | EVA | 55 | 950 |

When used to deliver a dental treatment composition to a person's teeth, and when it is desired to maximize adaptability, conformability and comfort, the disclosed dental trays will generally have a wall thickness less than about 1 mm, preferably in a range of about 0.03 mm to about 1 mm, more preferably in a range of about 0.05 mm to about 0.75 mm, and most preferably in a range of about 0.1 mm and about 0.5 mm.

Dental trays having a wall thickness greater than 1 mm are generally less comfortable and adaptable then the more preferred thinner walled dental trays. That is particularly true when using an elastomeric material having the same shore A hardness. Nevertheless, unlike thermoplastic materials used to make conventional dental trays and strips, the shore A hardness of elastomeric materials can be more easily manipulated (e.g., reduced) in order to yield thicker walled dental trays that can have high adaptability and conformability to a user's teeth. Hence, dental trays having a thickness greater than 1 mm, preferably less than about 1.5 mm, but which still exhibit high adaptability, conformability and comfort are within the scope of the invention.

The durometer hardness/softness of the elastomeric silicone or other elastomeric materials is advantageously selected to strike a balance between softness and wall thickness. Within the preferred wall thicknesses described above (i.e., about 0.03 mm to about 1 mm) the shore A durometer hardness value will preferably range from about 90 to about 20. Generally, a higher durometer value (less softness) is preferred when making thinner wall trays (e.g., in order to maintain good resiliency and spring-back properties), while lower durometer values (greater softness) are preferred with thicker wall trays (e.g., in order to maintain softness, high adaptability and comfort). For example, a tray with a wall thickness of about 0.25 mm may advantageously have a shore A durometer hardness value of about 40, while a tray with a wall thickness of about 0.1 mm may have a shore A durometer hardness value of about 70. On the other hand, a non-custom tray having a thickness of 1.5 mm may advantageously have a shore A hardness of about 10.

The elastic elongation of the elastomeric silicone or silicone-like tray materials disclosed herein is much greater than that of conventional non-elastomeric thermoplastic materials (e.g., EVA and/or PP) commonly used in forming non-custom trays. The elastic elongation of the elastomeric silicone or silicone-like material is preferably at least about 50%, more preferably at least about 75%, even more preferably at least about 100%, and most preferably at least about 300%. Accordingly to one embodiment, the elastic elongation is in a range of about 50% to about 2000%, preferably in a range of about 75% to about 1500%, more preferably in a range of about 100% to about 1000%, and most preferably in a range of about 300% to about 800%.

The dental treatment trays according to the invention can be manufactured by injection molding an uncured two-part liquid silicone composition into a mold cavity. In the case of liquid silicone rubber, the two parts are of relatively low viscosity (e.g., 1500-2000 Pa-s), which is significantly lower than the viscosity of thermoplastic materials traditionally used in molding a dental tray. As such, the injection pressures at which the material is injected into the mold are significantly lower (e.g., about 500 to about 5000 psi, typically about 2000 psi) than what are required when injection molding dental trays from commonly used non-elastomeric thermoplastic materials such as EVA, PCL, PVC, and other materials that have been used in injection molding dental trays (e.g., which are typically injected at a pressure of about 20,000 psi, and typically require the addition of a plasticizer in order to form thin wall trays). The greatly reduced pressures required to injection mold a tray from silicone compared to conventional thermoplastic materials greatly enhances the ability to manufacture trays having desired structural features, particularly at very small cross sections (i.e., less than 0.015 inch, or about 0.4 mm). Exemplary trays can be molded with relatively thin walls to achieve an acceptable degree of comfort for the user.

Although it is also possible to form elastomeric silicone or silicone-like dental trays with comparably thin walls (which may have the greatest comfort), this is not always necessary because a silicone or silicone-like dental tray of a given thickness exhibits greater comfort than a similarly-sized dental tray formed of non-elastomeric thermoplastic materials (e.g., a blend of EVA and PP). As such, a silicone or silicone like tray exhibiting comfort equal to or better than existing trays may have a wall thickness which is significantly greater. In effect, the use of elastomeric silicone or silicone-like materials allows a choice between a relatively thicker walled dental tray that is more easily and inexpensively formed, and which may not require an outer support tray during placement, and a thin-walled dental tray that provides a degree of comfort not found in a comparable tray formed of another material as a result of its thinness, adaptability, flexibility, elastic elongation, resiliency, and its soft and supple feel.

The dental treatment trays can be worn for any desired time period. Due to the extremely comfortable fit between the dental treatment trays and the person's teeth, they can be worn for extended periods of time as desired. The dental treatment trays can be worn for as little as a few minutes or as long as several hours. By way of example, not limitation, a typical treatment session of fast duration may last from about 10 to about 30 minutes; a treatment session of intermediate duration may last from about 30 minutes to about 2 hours; and a treatment session of long duration, including professional custom or overnight treatment while a person is sleeping, may last from about 2 hours to about 12 hours.

When used in combination with a sticky treatment composition, the disclosed dental treatment trays may be worn while performing normal daily activities, such as talking, drinking, smoking, coughing, smiling, frowning, grimacing, or while sleeping. Dental treatment trays according to the invention may be worn over a person's upper dental arch, lower dental arch, or both simultaneously.

Figure 4A:
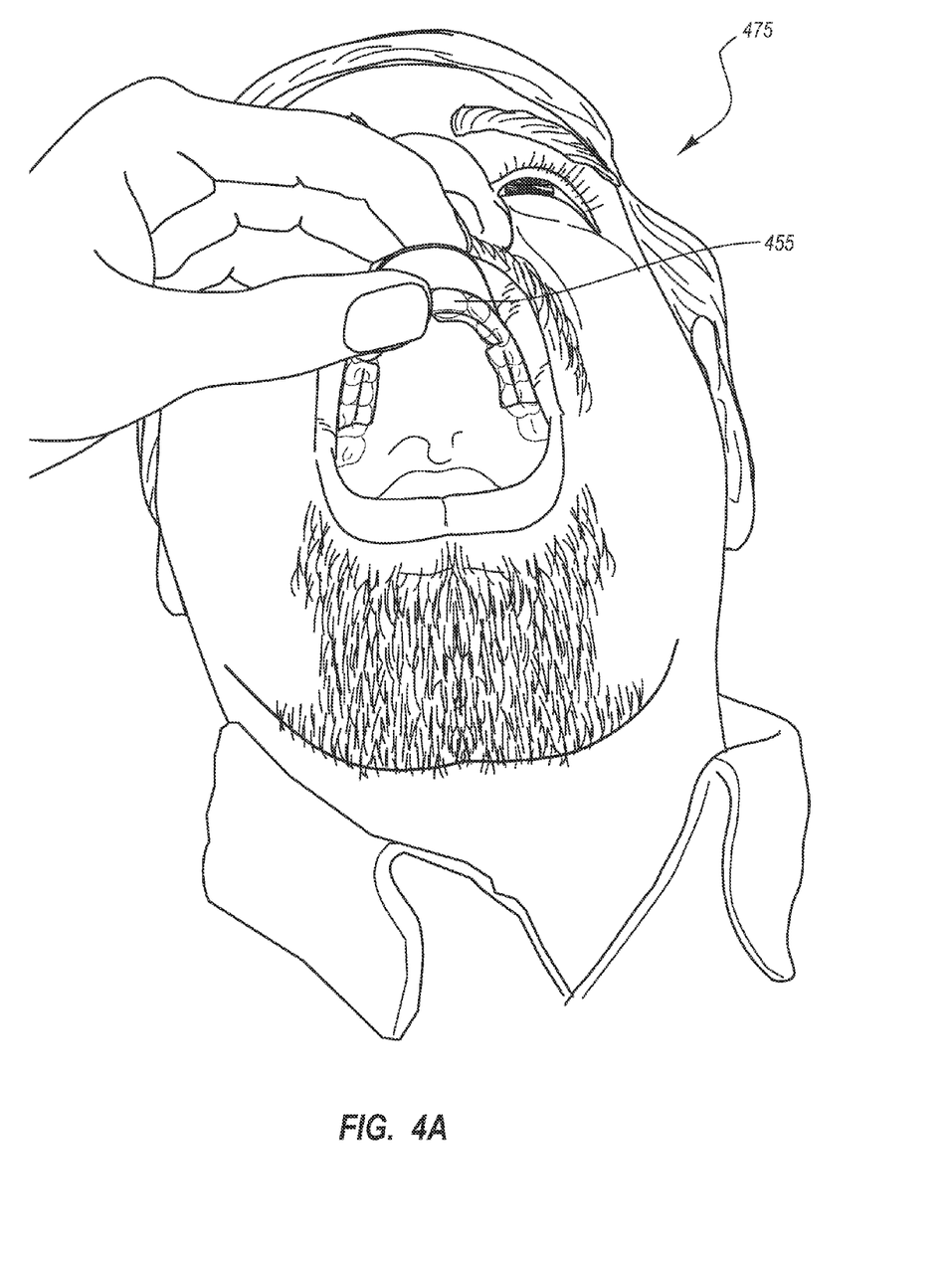
FIG. 4A illustrates a person placing a dental treatment tray according to the invention over the person's upper dental arch.
Figure 4B:
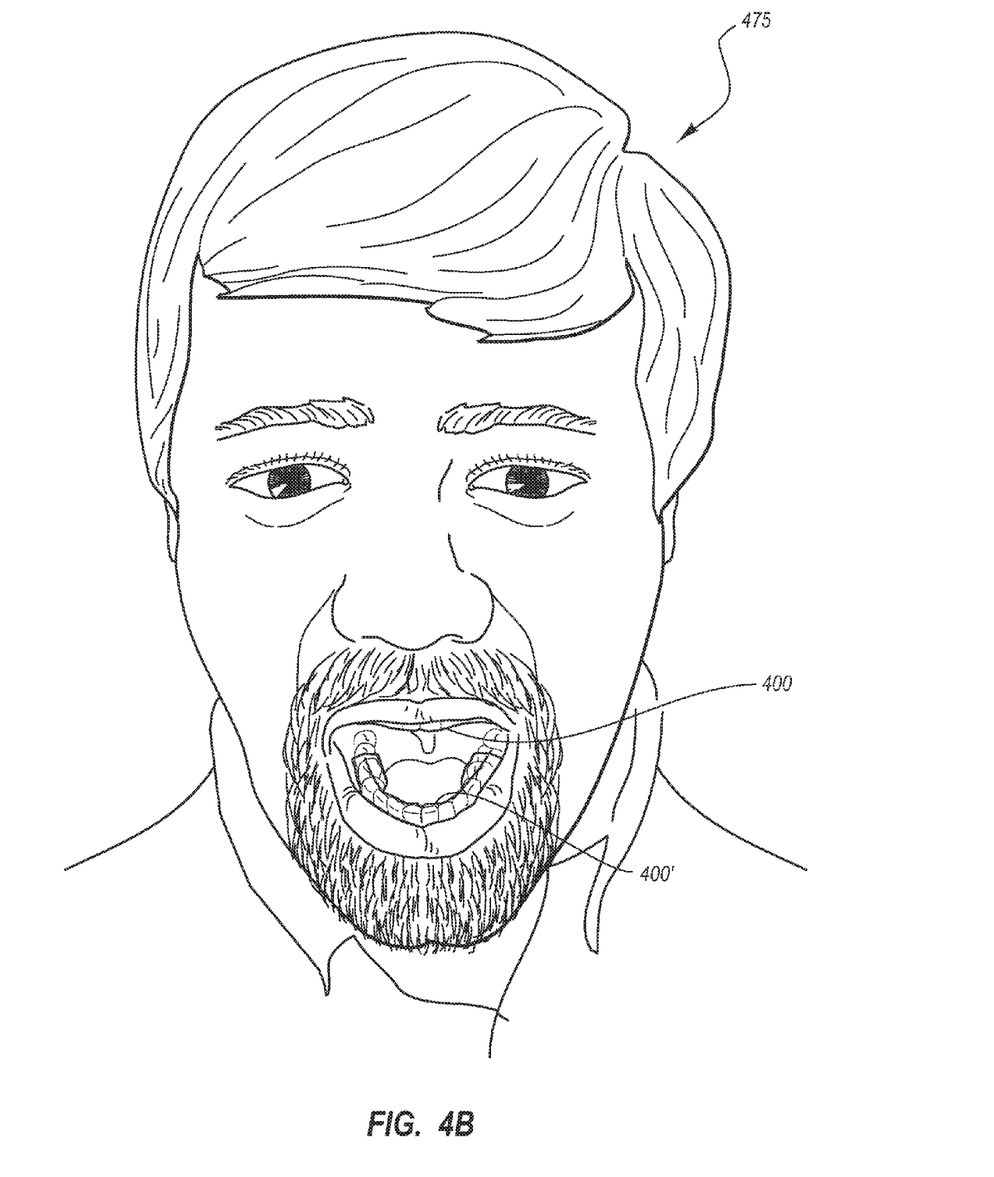
FIG. 4B illustrates dental treatment trays according to the invention in place over both the upper and lower dental arches.

FIG. 4A illustrates a person 475 placing a dental treatment assembly 455 over the person's upper dental arch. The outer support tray helps in placing the inner treatment tray over the teeth. FIG. 4B illustrates a dental treatment tray 400 in place over the person's upper dental arch and a dental treatment tray 400' over the lower dental arch, both outer support trays having been removed.

To remove the dental treatment tray after a desired time period, the user simply grasps a corner or portion of the tray and pulls it off the teeth. Any residual treatment composition that remains adhered to the person's teeth can be removed by washing or flushing with water and/or by brushing.

III. Examples

Following are examples of two-part silicone compositions and elastomeric silicone-like TPE compositions that have been or can be used to manufacture dental treatment trays according to the invention by injection molding. The exemplary formulations and manufacturing conditions are given by way of example, and not by limitation. Unless otherwise indicated, all percentages are by weight.

Example 1

A composition for injection molding a silicone dental treatment tray was formed from Shin-Etsu's KEG2000-50A/B two part thermoset silicone material. Part A containing the activator/hardener had a viscosity of about 1700 Pa-s, while part B containing the siloxane had a viscosity of about 1600 Pa-s.

The two parts of the silicone composition were pumped out of storage drums through hoses to a static mixing head where the two parts were mixed together. The mixed silicone material exited the static mixer and was forced into the screw and barrel of the injection molding machine. The mixed silicone material was injected into the heated mold (e.g., about 375° F.), at which point the material quickly polymerized. The tray was removed from the heated mold after polymerization was substantially complete, which occurred after about 30 seconds (i.e., 30 seconds±10 seconds). Exemplary formed trays exhibited excellent adaptability, flexibility, elastic elongation, and softness, while also being resilient. The molded trays were translucent, had a Shore A durometer hardness of about 50, and an elastic elongation of about 580%. Trays having wall thicknesses of about 0.004 inch (0.10 mm), about 0.006 inch (0.15 mm), about 0.008 inch (0.2 mm), about 0.01 inch (0.25 mm) and about 0.014 inch (0.36 mm), respectively, were formed. The trays were found to be very comfortable when worn over a person's dental arch, with better adaptability, flexibility, elastic elongation, softness, and resiliency as compared to a tray formed of materials (e.g., a blend of EVA and PP) that do not exhibit properties (e.g., particularly elastic elongation, softness, and resiliency) similar to elastomeric silicone. In addition, the silicone material surface exhibited a tendency to adhere (i.e., grip) to tooth surfaces.

Example 2

A composition for injection molding a dental treatment tray was formed from SEBS TPE 45A material. The heated material was pumped so as to be forced into the screw and barrel of the injection molding machine. The material was injected into the mold and then cooled. The cooled tray was removed from the mold, which occurred after about 30 seconds (i.e., 30 seconds±10 seconds). Exemplary trays formed from SEBS exhibited excellent adaptability, flexibility, elastic elongation, and softness, while also being resilient, similar to the silicone tray of Example 1. The molded trays were translucent, had a Shore A durometer hardness of about 45, an elastic elongation of about 800%, and a wall thickness of about 0.020 inch (0.5 mm). The trays were found to be very comfortable when worn over a person's dental arch, with better adaptability, flexibility, elastic elongation, softness, and resiliency as compared to a conventional non-custom tray formed of materials that do not exhibit properties (e.g., particularly elastic elongation, softness, and resiliency) similar to elastomeric silicone. In addition, the SEBS material surface exhibited a tendency to adhere (i.e., grip) to tooth surfaces.

Example 3

A composition for injection molding a dental treatment tray was formed from VERSAFLEX CL30. The heated TPE material was pumped so as to be forced into the screw and barrel of the injection molding machine. The material was injected into the mold. The cooled tray was removed from the mold. Exemplary formed VERSAFLEX CL30 trays exhibit excellent adaptability, flexibility, elastic elongation, and softness, while also being resilient, similar to the silicone tray of Example 1. The molded trays are translucent, have a Shore A durometer hardness of about 30, an elastic elongation of about 780%, and a wall thickness of about 0.020 inch (0.5 mm). The trays are very comfortable when worn over a person's dental arch, with better adaptability, flexibility, elastic elongation, softness, and resiliency as compared to a tray formed of materials that do not exhibit properties (e.g., particularly elastic elongation, softness, and resiliency) similar to silicone. In addition, the VERSAFLEX CL30 material surface exhibits a tendency to adhere (i.e., grip) to tooth surfaces.

Example 4

A composition for injection molding a dental treatment tray was formed from VERSAFLEX CL40. The heated TPE material was pumped so as to be forced into the screw and barrel of the injection molding machine. The material was injected into the mold. The cooled tray was removed from the mold. Exemplary formed VERSAFLEX CL40 trays exhibit excellent adaptability, flexibility, elastic elongation, and softness, while also being resilient, similar to the silicone tray of Example 1. The molded trays are translucent, have a Shore A durometer hardness of about 40, an elastic elongation of about 690%, and a wall thickness of about 0.020 inch (0.5 mm). The trays are very comfortable when worn over a person's dental arch, with better adaptability, flexibility, elastic elongation, softness, and resiliency as compared to a tray formed of materials that do not exhibit properties (e.g., particularly elastic elongation, softness, and resiliency) similar to silicone. In addition, the VERSAFLEX CL40 material surface exhibits a tendency to adhere (i.e., grip) to tooth surfaces.

Examples 5-27

Dental treatment trays were formed from each of the elastomeric silicone or silicone-like materials listed in the table below. The trays generally exhibited excellent adaptability, flexibility, elastic elongation, and softness, while also being resilient, similar to the silicone tray of Example 1. The molded trays had a wall thickness of about 0.020 inch (0.5 mm) and a Shore A durometer hardness and elasticity (i.e., % elongation) as listed in the table below. The trays are very comfortable when worn over a person's dental arch, with better adaptability, flexibility, elastic elongation, softness, and resiliency as compared to trays formed of materials that do not exhibit properties (e.g., particularly elastic elongation, softness, and resiliency) similar to silicone.

| Ethanol | 31.95% |
|---|---|
| Water | 10% |
| Polyvinyl Pyrrolidone (M.W. = 1.3 million) | 27% |
| Polyvinyl Pyrrolidone (M.W. of about 60,000) | 10% |
| Sodium Laurel Sulfate | 0.5% |
| Glycerine | 15% |
| Sucralose 25% solution | 0.5% |
| Peach Flavor | 4% |
| Potassium Nitrate | 0.8% |
| Sodium Fluoride | 0.25% |

The resulting composition was spread over the surface of a dental tray and then dried so as to form a substantially solid treatment composition. The treatment composition was initially dry to the touch, but became very sticky when contacted with water or saliva during use. The potassium nitrate provided a dental desensitizing effect. The sodium fluoride provided both a desensitizing and remineralizing effect. The trays reliably adhered to tooth tissue, and exhibited excellent comfort and adhesiveness.

Example 29

A sticky, viscous dental bleaching composition was prepared by mixing together the following components:

| Water | 22.5% |
|---|---|
| EDTA Disodium | 0.1% |
| Carbamide Peroxide | 18.5% |

| Example | Manufacturer | Product | Product Type | Shore A Hardness | % Elongation |
|---|---|---|---|---|---|
| 5 | Shin-Etsu | SVX-19550C-7 | Silicone | 50 | 640 |
| 6 | Wittenburg B.V. | MT 970 | SEBS | 70 | |
| 7 | Wittenburg B.V. | Cawiton PR 2677F | SEBS | 25 | |
| 8 | Teknor Apex | MP 1870-1000 | SEBS-TPE | 70 | 600 |
| 9 | Bayer | Texin 985 | TPE (Polyether) | 86 | 500 |
| 10 | Bayer | Texin 285 Natural | TPE (Polyether) | 85 | 500 |
| 11 | Bayer | Texin 1201 | TPE | 67 | 300 |
| 12 | GLS Corp. | Versaflex 2250 | TPE | 50 | 760 |
| 13 | GLS Corp. | Versalloy 9055X-1 | TPE | 53 | 590 |
| 14 | GLS Corp. | Dynaflex G2701-1000-02 | TPE | 66 | 590 |
| 15 | GLS Corp. | Dynaflex G 2703-1000-02 | TPE | 58 | 690 |
| 16 | Dow Corning | TPSiV 3010 | TPE | 50 | 470 |
| 17 | Dow Corning | TPsiV 3040-55A | TPE | 55 | 450 |
| 18 | Dow Corning | LSR C6-550 | Silicone | 55 | 661 |
| 19 | Dow Corning | LSR C6-570 | Silicone | 70 | 442 |
| 20 | Dow Corning | Silastic Dev SB 2% bleed | Silicone | 50 | 450 |
| 21 | JRS | Excelink 1600B | TPE | 56 | 640 |
| 22 | PolyOne | Elastamax EG-9065 | TPE | 65 | 420 |
| 23 | Advance Polymers | Duragrip DGR 6250 CL | TPE | 50 | 800 |
| 24 | Elastocon | Elastocon 2840 | TPE | 40 | 580 |
| 25 | Elastocon | Elastocon 2855 | TPE | 55 | 660 |
| 26 | Kraiburg | Thermolast TF4THT | TPE | 40 | 610 |
| 27 | Kraiburg | Thermolast TF5THT | TPE | 50 | 680 |

Following are examples of dental treatment compositions that can be used in combination with the trays disclosed herein.

Example 28

An initially flowable composition suitable for use in manufacturing a substantially solid treatment composition was formed by mixing together the following components:

-continued

| Sucralose 25% solution | 0.75% |
|---|---|
| Glycerine | 41.6% |
| Carbopol 974 | 5.3% |
| Sodium Hydroxide 50% solution | 2.25% |
| Polyvinyl Pyrrolidone (M.W. = 1.3 million) | 2% |
| Carboxymethyl Cellulose | 4% |
| Watermelon Flavor | 3% |

A bead of dental bleaching composition was spread along the buccal-labial side wall of a silicone or silicone-like dental treatment tray according to the invention. Alternatively, the dental bleaching composition is placed over a substantially solid adhesive composition preloaded within a dental treatment tray. The trays reliably adhere to tooth tissue, and exhibit excellent comfort and adhesiveness.

Additional exemplary dental treatment compositions, and methods for making such compositions, which may be used with devices according to the invention are disclosed in U.S. Pat. No. 5,376,006; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368, 576; U.S. Pat. No. 6,387,353; U.S. Pat. No. 6,500,408; U.S. Pat. No. 6,503,485 and U.S. patent application Ser. No. 11/460,016 filed Jul. 26, 2006. For purposes of disclosing dental treatment compositions, and methods of making such compositions, the foregoing patents and application are incorporated herein by reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A non-customized dental treatment tray for use in applying a dental treatment composition to a person's teeth and/or gums and which is highly adaptable in order to approximate the comfort and fit of a customized dental tray, comprising:
a non-customized barrier layer formed from a moisture-resistant elastomeric material in the shape of a dental tray, wherein the non-customized barrier layer is devoid of structures corresponding to the size and shape of a person's unique dentition so as to comfortably fit over a plurality of differently-sized and shaped teeth and dental arches corresponding to different people,
wherein the elastomeric material consists essentially of cured elastomeric silicone and optionally less than about 10% by weight of an auxiliary component,
wherein the elastomeric material has an elastic elongation of at least about 50%, and
wherein the non-customized barrier layer is soft, flexible and elastically deformable in order to be highly adaptable so that, when placed over a person's teeth during use, the non-customized barrier layer adapts and at least partially conforms to unique ridges, depressions and contours of the person's teeth.

2. A non-customized dental treatment tray as recited in claim 1, wherein the elastomeric material has an elastic elongation of at least about 75%.

3. A non-customized dental treatment tray as recited in claim 1, wherein the elastomeric material has an elastic elongation of at least about 100%.

4. A non-customized dental treatment tray as recited in claim 1, wherein the elastomeric material has an elastic elongation of at least about 300%.

5. A non-customized dental treatment tray as recited in claim 1, wherein the barrier layer has a cross-sectional thickness of less than about 1 mm.

6. A non-customized dental treatment tray as recited in claim 5, wherein the elastomeric material has a shore A durometer hardness value in a range of about 20 to about 90.

7. A non-customized dental treatment tray as recited in claim 1, wherein the barrier layer has a cross-sectional thickness in a range of about 1 mm to about 1.5 mm.

8. A non-customized dental treatment tray as recited in claim 7, wherein the elastomeric material has a shore A durometer hardness value of less about 20.

9. A non-customized dental treatment tray as recited in claim 1, wherein the barrier layer includes a buccal-labial side wall and a bottom wall adjacent the buccal-labial side wall, the buccal-labial side wall and the bottom wall defining a hollow interior into which a dental composition may be placed.

10. A non-customized dental treatment tray or strip as recited in claim 1, wherein the barrier layer has a cross-sectional thickness of less than about 0.75 mm.

11. A non-customized dental treatment tray or strip as recited in claim 1, wherein the barrier layer has a cross-sectional thickness of less than about 0.5 mm.

12. A non-customized dental treatment tray as recited in claim 1, wherein the non-customized dental tray is formed by injection molding an initially uncured silicone resin to form a tray intermediate and then curing the silicone resin to form the non-customized dental tray comprising the cured elastomeric silicone.

13. A non-customized dental treatment tray as recited in claim 12, wherein the non-customized dental treatment tray has outer edges which are smooth and rounded.

14. A dental treatment tray or strip as recited in claim 1, wherein the elastomeric material is blended with at least one auxiliary component selected from the group consisting of latexes, nitriles, water, plasticizers, colorants, and flavorants, and wherein any included latex, nitrile, water, plasticizer, colorant and/or flavorant collectively comprises less than about 3% by weight of the elastomeric material.

15. A dental treatment device comprising:
a non-customized dental treatment tray as recited in claim 1; and
a dental treatment composition positioned adjacent to the non-customized barrier layer.

16. A dental treatment device as recited in claim 15, wherein the dental treatment composition is hydrophilic.

17. A non-customized dental treatment tray for use in applying a dental treatment composition to a person's teeth and/or gums and which is highly adaptable in order to approximate the comfort and fit of a customized dental tray, comprising:
a non-customized tray body formed from a thermoset elastomeric material and which is devoid of structures corresponding to the size and shape of a person's unique dentition so as to comfortably fit over a plurality of differently-sized and/or shaped teeth corresponding to different people,
wherein the thermoset elastomeric material consists essentially of cured elastomeric silicone and optionally less than about 10% by weight of an auxiliary component,
wherein the elastomeric material has an elastic elongation of at least about 100%, and
wherein the non-customized tray body has a cross-sectional thickness of less than about 1.5 mm and is soft, flexible and elastically deformable in order to be highly adaptable so that, when placed over a person's teeth during use, the non-customized tray body adapts and at least partially conforms to unique ridges, depressions and contours of the person's teeth.

18. A non-customized dental treatment tray as recited in claim 17, wherein the non-customized tray body has a thickness of less than about 0.5 mm and wherein the cured elastomeric silicone has an elastic elongation of at least about 300%.

19. A non-customized dental treatment tray for use in applying a dental treatment composition to a person's teeth and/or gums and which is highly adaptable in order to approximate the comfort and fit of a customized dental tray, comprising:
   a non-customized tray body formed from a elastomeric material and which is devoid of structures corresponding to the size and shape of a person's unique dentition so as to comfortably fit over a plurality of differently-sized and/or shaped teeth corresponding to different people,
   wherein the elastomeric material consists essentially of cured elastomeric silicone and optionally less than about 3% by weight of a plasticizer or other auxiliary component,
   wherein the elastomeric material has an elastic elongation of at least about 300% and is thermally stable at temperatures of up to at least about 100° C. so as to not be customizable by heating in water and then permanently registering a person's unique dentition into the heated tray body, and
   wherein the non-customized tray body has a cross-sectional thickness of less than about 1.5 mm and is soft, flexible and elastically deformable in order to be highly adaptable so that, when placed over a person's teeth during use, the non-customized tray body adapts and at least partially conforms to unique ridges, depressions and contours of the person's teeth.

20. A non-customized dental treatment tray as recited in claim 19, wherein the non-customized tray body has a thickness of less than about 0.5 mm and wherein the thermoplastic elastomeric material has an elastic elongation of at least about 300%.

* * * * *

UNITED STATES PATENT AND TRADEMARK OFFICE
CERTIFICATE OF CORRECTION

| | |
|---|---|
| PATENT NO. | : 8,202,091 B2 |
| APPLICATION NO. | : 12/201902 |
| DATED | : June 19, 2012 |
| INVENTOR(S) | : Lewis et al. |

It is certified that error appears in the above-identified patent and that said Letters Patent is hereby corrected as shown below:

In the Specifications:

Column 9
Line 44, change "Bottom wall 204" to --Bottom wall 208--

Column 13
Line 40, change "then" to --than--

Column 15
Line 7, change "silicone like" to --silicone-like--

In the Claims:

Column 19
Line 40, change "differently-sized" to --differently sized--

Signed and Sealed this
Fourteenth Day of May, 2013

Teresa Stanek Rea
*Acting Director of the United States Patent and Trademark Office*